US009874507B2

United States Patent
Dingman et al.

(10) Patent No.: US 9,874,507 B2
(45) Date of Patent: Jan. 23, 2018

(54) SYSTEMS, APPARATUSES, AND METHODS FOR MEASURING SUBMERGED SURFACES

(71) Applicant: Delta SubSea LLC, Montgomery, TX (US)

(72) Inventors: Scott P. Dingman, Montgomery, TX (US); Roger Warnock, Tomball, TX (US); Alessandro Vagata, Richmond, TX (US)

(73) Assignee: Delta Subsea, LLC, Montgomery, TX (US)

( * ) Notice: Subject to any disclaimer, the term of this patent is extended or adjusted under 35 U.S.C. 154(b) by 0 days.

(21) Appl. No.: 15/141,269

(22) Filed: Apr. 28, 2016

(65) Prior Publication Data

US 2016/0320282 A1 Nov. 3, 2016

Related U.S. Application Data

(60) Provisional application No. 62/153,944, filed on Apr. 28, 2015.

(51) Int. Cl.
*G01V 5/00* (2006.01)
*G01N 11/04* (2006.01)
(Continued)

(52) U.S. Cl.
CPC ............. *G01N 11/04* (2013.01); *B63G 8/001* (2013.01); *G01N 9/24* (2013.01); *G01N 23/12* (2013.01);
(Continued)

(58) Field of Classification Search
CPC .................. G01N 23/18; G01N 23/02
See application file for complete search history.

(56) References Cited

U.S. PATENT DOCUMENTS 3,753,091 A * 8/1973 Daspit .................... G01N 27/83
324/526
3,787,683 A * 1/1974 Kishel .................... G01N 23/12
250/308
(Continued)

FOREIGN PATENT DOCUMENTS

| GB | 2200206 | 7/1988 |
| GB | 2496736 | 5/2013 |
| JP | 2001289825 A | * 10/2001 |

OTHER PUBLICATIONS

Camerini et al., "A robot for offshore pipeline inspection," 2010, 9th IEEE/IAS International Conference on Industry Applications, 6 pages.*

(Continued)

*Primary Examiner* — Kiho Kim
(74) *Attorney, Agent, or Firm* — Jason P. Mueller; Adams & Reese LLP (57) ABSTRACT

The present disclosure provides systems, apparatuses, and methods for measuring submerged surfaces. Embodiments include a measurement apparatus including a main frame, a source positioned outside a pipe and connected to the main frame, and a detector positioned outside the pipe at a location diametrically opposite the source and connected to the main frame. The source may transmit a first amount of radiation. The detector may receive a second amount of radiation, determine a composition of the pipe based on the first and second amounts of radiation, and send at least one measurement signal. A control canister positioned on the main frame or on a remotely operated vehicle (ROV) attached to the apparatus may receive the at least one measurement signal from the detector and convey the at least one measurement signal to software located topside.

26 Claims, 8 Drawing Sheets

(51) Int. Cl.
*G01N 23/12* (2006.01)
*B63G 8/00* (2006.01)
*G01N 9/24* (2006.01)
*G05D 1/00* (2006.01)

(52) U.S. Cl.
CPC ......... *G05D 1/0011* (2013.01); *G05D 1/0088* (2013.01); *B63G 2008/005* (2013.01); *G01N 2223/1013* (2013.01); *G01N 2223/308* (2013.01); *G01N 2223/631* (2013.01)

(56) References Cited

U.S. PATENT DOCUMENTS

| | | | | |
|---|---|---|---|---|
| 4,309,606 A * | 1/1982 | Bjorkman | ............ | G01B 15/025 250/252.1 |
| 4,461,354 A * | 7/1984 | Buras | ............ | E21B 19/16 166/343 |
| 4,795,903 A * | 1/1989 | Clayton | ............ | G01N 23/12 250/301 |
| 4,866,745 A * | 9/1989 | Akai | ............ | A61B 6/032 378/10 |
| 5,507,596 A * | 4/1996 | Bostelman | ............ | B63B 38/00 166/355 |
| 5,583,904 A * | 12/1996 | Adams | ............ | G01N 23/046 378/22 |
| 5,698,854 A * | 12/1997 | Gupta | ............ | G01N 23/18 250/358.1 |
| 6,240,160 B1 * | 5/2001 | Daaland | ............ | F17D 5/00 138/132 |
| 7,402,796 B2 * | 7/2008 | Fitzgerald | ............ | G01F 1/74 250/253 |
| 8,759,780 B2 * | 6/2014 | Dobbs | ............ | G01B 15/02 250/360.1 |
| 8,767,912 B1 * | 7/2014 | Alzaidi | ............ | G01B 15/02 250/268 |
| 2005/0041775 A1 * | 2/2005 | Batzinger | ............ | G01N 23/18 378/59 |
| 2009/0149776 A1 * | 6/2009 | Adams | ............ | A61B 5/0059 600/584 |
| 2011/0168900 A1 * | 7/2011 | Dobbs | ............ | G01B 15/02 250/360.1 |
| 2012/0223813 A1 * | 9/2012 | Baxter | ............ | E21B 44/00 340/10.1 |
| 2015/0367387 A1 * | 12/2015 | Alcuri | ............ | G01N 17/008 405/184.1 |

OTHER PUBLICATIONS

Alam et al., "Practical Application of an Evolutionary Algorithm for the Design and Construction of a Six-inch Submarine", Proceedings of the 2014 IEEE Congress on Evolutionary Computation, XP032644612, pp. 2825-2832, Jul. 6, 2014.

Reber et al., "Inspection of Pipelines Through Thick Coating", Proceedings of the 2014 Pigging Products & Services Association Seminar, XP055284238, pp. 9-1-9-8, Nov. 19, 2014.

Robins, "Tracero Discovery: The world's first subsea CT scanner for pipeline integrity and flow assurance visualisation", http://www.subseauk.com/documents/presentations/tracero discovery presentation, subsea asia 2014.pdf, XP055284167, pp. 1-48, Jun. 11, 2014.

* cited by examiner

SYSTEMS, APPARATUSES, AND METHODS FOR MEASURING SUBMERGED SURFACES

This application claims the benefit of U.S. Provisional Patent Application No. 62/153,944, filed Apr. 28, 2015, which is incorporated herein by reference.

DESCRIPTION OF EMBODIMENTS

A submerged or submarine pipeline is a pipeline passing under water, which is typically laid on a seabed, or inside a trench below the seabed. The pipeline may also be located partially on-land. Submarine pipelines are used primarily to carry oil or gas but may also be used to transport other materials.

Plugging by hydrates and/or other media in pipelines is one of the major flow assurance challenges facing the oil and gas industry because it prevents the flow of media in the pipeline and causes substantial interruption and losses in operations. As oil and gas production moves into harsh and challenging environments, including deep subsea environments, there is a growing need to prevent this plug formation.

The value of remediation methods for plug formation depends on the speed and efficiency in locating an accumulation or plug in the pipeline. The media flowing in the pipeline, including gas, oil, wax, asphaltene, hydrates, paraffin, and sand have varied and/or minimal differences in their respective densities and composition. Detecting these differences in densities and composition allows for the ability to locate total or partial blockage in the pipe. A way to detect these differences in densities is by the use of radiation to measure the density of the contents of the pipeline. Methods of using radiation, including gamma rays, to determine the density of pipelines (including to measure flow and hold-up in the pipelines) are disclosed in U.S. Pat. No. 7,402,796, U.S. Pat. No. 4,795,903, U.S. Pat. No. 4,667,515, U.S. Patent Pub. No. 2012/0087467 A1, and U.S. Patent Pub. No. 2008/0137808 A1, all of which are incorporated herein by reference. These methods include placing a "source" of radiation outside a pipeline for directing radiation from the source through a portion of the pipeline, and placing a "detector" at a location outside the pipeline opposite the source of radiation for detecting the radiation and measuring the density of the pipeline. The amount of radiation which subsequently exits the pipeline depends upon the mass of the media contained within the pipeline and its ability to absorb radiation. Thus, a reduction in the amount of radiation which reaches the detector indicates an increased bulk density of the media flowing through or contained within the pipeline as more radiation is absorbed by the media.

The primary existing tool providing for inspection of submerged pipelines in subsea environments is the "Discovery" tool provided by Tracerco™. This tool, however, is extremely complex, and functions by making a tomography of the pipeline. Each measurement of a "slice" of the pipeline takes about 20 minutes. The tool is also very heavy (approximately two tons) and requires dredging around the pipeline to be operated. Additionally, operation of the tool is very expensive and time-consuming, and requires the use of additional complex subsea operations.

Embodiments of the present disclosure relate generally to non-destructive measuring systems, apparatuses, and methods, and in particular though non-limiting embodiments, to systems, apparatuses and methods for measuring submerged pipelines.

The present disclosure provides improved apparatuses, systems, and methods for the measurement of submerged surfaces, including measurement of submerged pipelines. The disclosed embodiment includes a measurement apparatus having a source/emitter and a detector connected to a main frame and configured to detect density and/or composition of a section of pipeline. The measurement apparatus may be configured for attachment to an ROV. The attachment to the ROV may be through a hydraulic and/or electrical system.

According to exemplary embodiments of the present disclosure, methods are provided for measuring submerged pipelines. Steps may include connecting a measurement apparatus to an ROV, and using the ROV to lower and place the apparatus upon a submerged pipeline such that the apparatus securely fits on the pipeline. A source and a detector of the apparatus may then be used to measure the density and/or composition of the section of the submerged pipeline and create an at least one measurement signal. The at least one measurement signal may then be sent via software on the apparatus to software on the ROV and/or to software located topside. This improved method of measurement of submerged pipelines may be performed in ranges of approximately 3,000 meters to 4,700 meters below sea level.

The measurement apparatus may be moved along the submerged pipeline as needed using the ROV. Exemplary embodiments of the present disclosure may include traction rollers and/or crawlers and/or wheels attached to the apparatus, allowing the apparatus to move along the pipe. The rollers and/or crawlers and/or wheels may be powered by electric or hydraulic motors. The rollers and/or crawlers and/or wheels may be arranged such that the main frame of the apparatus is in close proximity to an outer surface of the section of pipe without scraping or contacting the surface. The number of rollers and/or crawlers and/or wheels may vary in different embodiments of the disclosure. The rollers and/or crawlers and/or wheels may allow for quick and efficient guidance of the measurement apparatus along the pipeline by an ROV. Exemplary embodiments of the present disclosure may also include a stabilizing system including a brick of lead positioned within the main frame of the apparatus to act as a ballast assist in maintaining the stability of the apparatus along the pipe. The apparatus may also include a handle allowing for ROV-assisted manipulation of the measurement apparatus along the pipe.

Embodiments of the present disclosure therefore allow for miles of pipeline to be measured in a single day. The measurement apparatus may be securely and quickly guided along the pipeline using the connection to the ROV. The measurement apparatus may be employed to measure vast sections of pipeline for potential problem areas. In this way, the present disclosure allows for efficient, low cost measurement of the pipeline. Although discussed herein in conjunction with pipelines, the measurement apparatus may be used on vessels or other surfaces.

Embodiments of the present disclosure provide for measuring the content of submerged surfaces, including submerged pipelines, in a more efficient manner that does not affect the measured material, requires less process downtime for installation, is non-intrusive, and is easily deployable. Embodiments of the present disclosure provide for a faster, cheaper, and more reliable method for diagnosing flow abnormalities due to partial or total plugs within pipelines without substantial interruption to pipeline operations.

Figure 1:
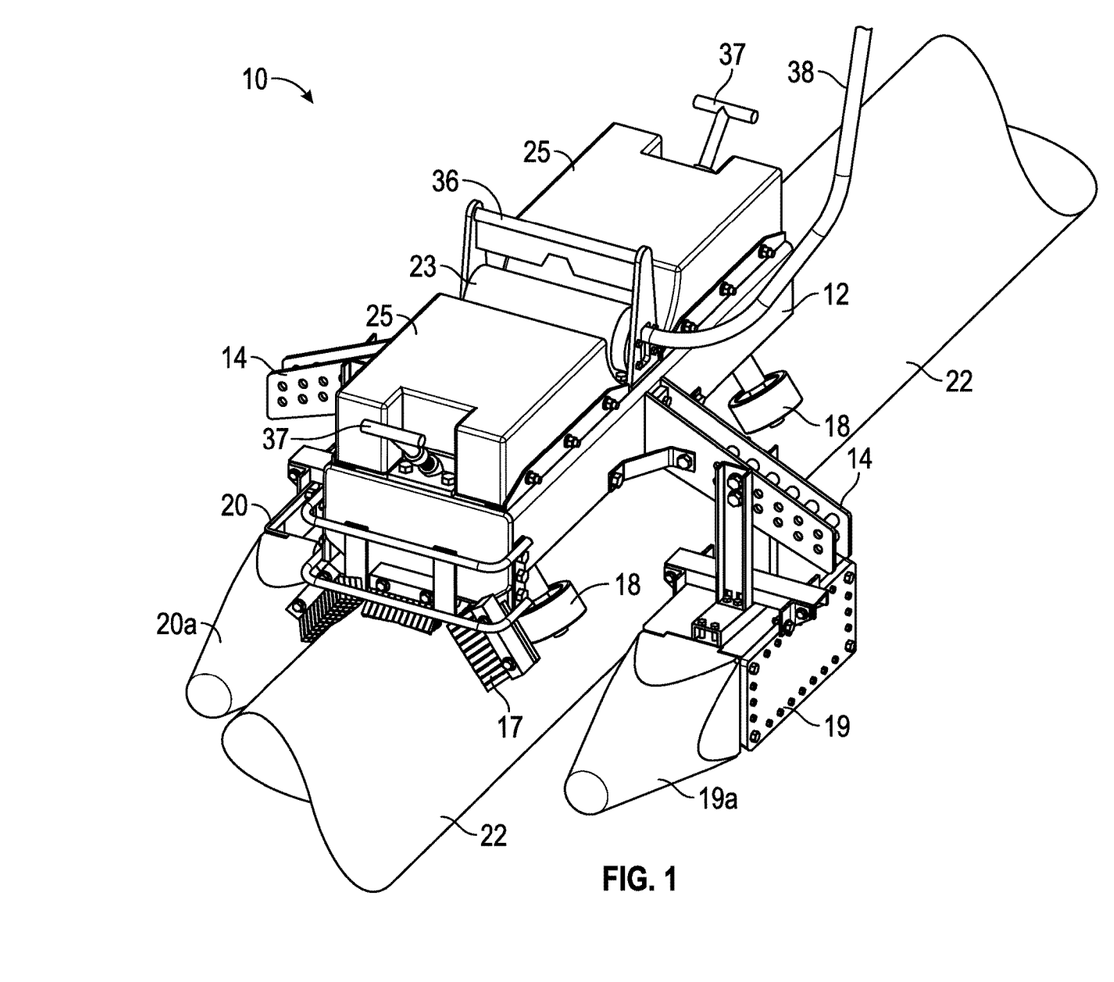
FIG. 1 is an isometric view of a measurement apparatus positioned on a section of pipe, according to an exemplary embodiment of the present disclosure.
Figure 2:
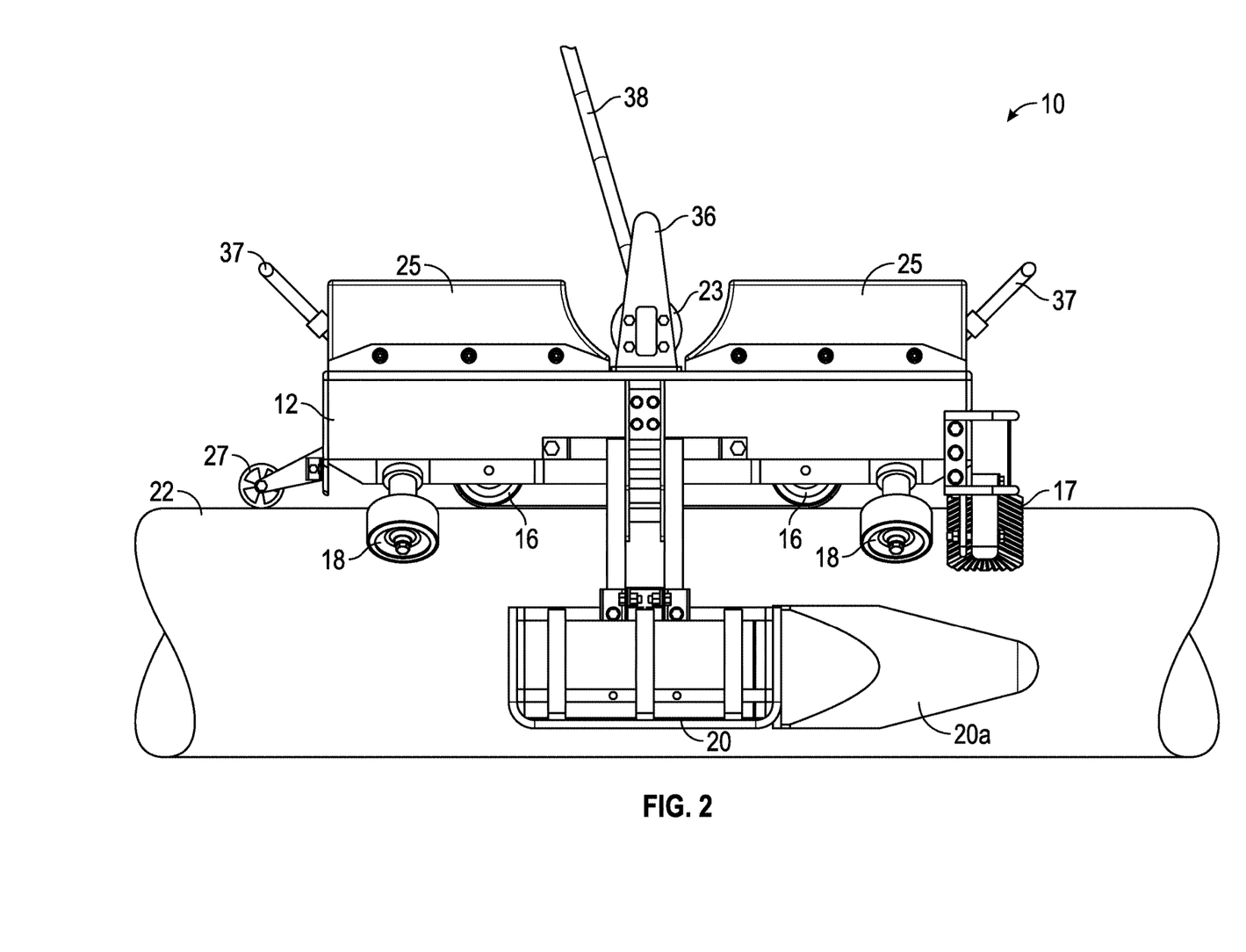
FIG. 2 is a side view of the measurement apparatus shown in FIG. 1.
Figure 3:
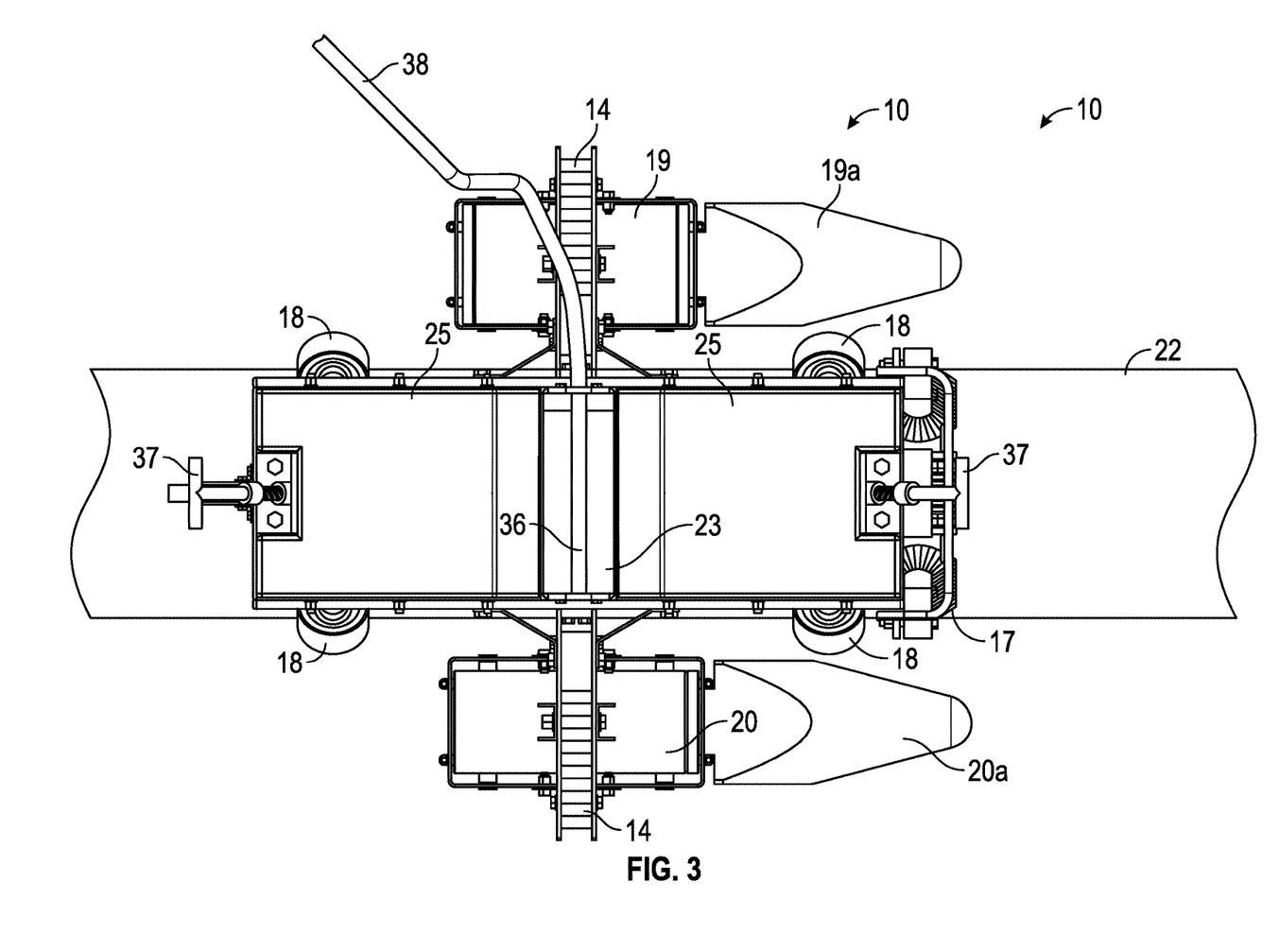
FIG. 3 is a top view of the measurement apparatus shown in FIG. 1.

Referring to FIGS. 1 to 3, different views of a measurement apparatus 10 are shown. In FIG. 1, an exemplary embodiment of a measurement apparatus 10 positioned on a section of pipe 22 is shown. Measurement apparatus 10 may include a main frame 12, a radiation source 19 connected to the main frame 12, and a radiation detector 20 connected to the main frame 12. In an exemplary embodiment, the main frame 12 may have a rectangular shape. In alternative embodiments, the main frame 12 may have other shapes suitable for the measurement functions of the apparatus 10. In an exemplary embodiment, the main frame 12 may be made of aluminum. However, the main frame 12 may be made of other materials suitable for the measurement functions of the apparatus 10. In particular embodiments, the apparatus 10 may perform measurements on a section of pipe 22 with a diameter of approximately ten to eighteen inches. However, the apparatus 10 may also perform measurements on pipes with larger or smaller diameters. In exemplary embodiments, the apparatus 10 may weigh approximately 150 pounds in water and 380 pounds in air, which is substantially less than existing measurement apparatuses performing similar functions.

In various embodiments, source 19 and/or detector 20 may be positioned outside the pipe 22 and connected to the main frame 12. In an exemplary embodiment, both source 19 and/or detector 20 may be connected to the apparatus 10 using an elongated support frame 14 having a plurality of grooves and tracks configured for attachment to vertical bars holding the source 19 and/or detector 20 in a secured carriage. See, e.g, FIG. 1. The vertical bars may be attached to the support frame 14 using mechanical attachments such as screws and/or bolts. Alternatively, other mechanical configurations may be used to attach the bars to the support frame 14, including circumferential straps, magnets, ties, quick releases, snap locks, or other combinations thereof, and/or other suitable systems. In alternative embodiments, source 19 and/or detector 20 may be connected to the main frame 12 using other suitable methods. In some embodiments, the support frame 14 may be connected to electrical or electro-hydraulic linear actuators or hydraulic cylinders, that may in turn be connected to the source 19 and/or detector 20, and configured to adjust the source 19 and/or the detector 20 in a direction perpendicular to the pipe 22. In an exemplary embodiment, the support frame 14 may be made of aluminum. Alternatively, the support frame 14 may be made of other materials suitable for attaching support frame 14 to the main frame 12 and securely holding the source 19 and/or detector 20 in place.

In particular embodiments, source 19 and/or detector 20 may each be attached to cleaning structures 19a, 20a configured to move debris away from the pipe 22 during measurement of the pipe 22. In exemplary embodiments, cleaning structures 19a, 20a may each have a cone shape to more efficiently move debris and other material away from the pipe 22. In alternative embodiments, cleaning structures 19a, 20a may have other shapes suitable for performing this function. Cleaning structures 19a, 20a may be attached to the front end, back end, and/or the sides of the source 19 and/or detector 20. In embodiments of the present disclosure, source 19 and/or detector 20 may be securely held in a source carriage and/or detector carriage, respectively. In an exemplary embodiment, the source carriage and/or detector carriage may be made of titanium, which is permeable to radiation.

Source 19 may include a radiation source contained within a radiation source holder and configured to transmit a continuous first amount of radiation through a section of the pipe 22. In exemplary embodiments, this first amount of radiation may be gamma rays. In this embodiment, the radiation is generally a radioactive isotope as used in conventional (single source and detector) density gauges where the radiation source is commonly 662 keV gamma radiation (approximately 100-200 millicurie) from a cesium-137 isotope ($^{137}$Cs). Alternatively, this first amount of radiation may be derived from other radioactive sources, including X-rays. In exemplary embodiments, source holder of source 19 may be at least one of the SHLD, SHF, SHLG, SHLM, and SR source holders for radiation-based measurement offered by VEGA Americas, Inc.

Source 19 may be positioned at a location outside the pipe 22. Source 19 may include a collimator to direct the first amount of radiation towards the pipe 22. In exemplary embodiments, source 19 may also include a shutter to open or close the collimator. In this embodiment, source 19 may include electric motors to activate the shutter, i.e., turn the shutter on and off and let out radiation as needed. Particularly, source 19 may use a solenoid to achieve this function. In alternative embodiments, source 19 may include an electrical linear actuator and/or hydraulic cylinder and/or other suitable devices to achieve this function. If the shutter is on, the first amount of radiation will be transmitted from the source 19 using the collimator. If the shutter is off, the first amount of radiation will not be transmitted from the source 19. In alternative embodiments, source 19 may include other available methods to transmit and/or direct the radiation towards the pipe 22. In a particular embodiment, source 19 may weigh approximately sixty pounds.

Detector 20 may be positioned outside a section of the pipe 22 at a location diametrically opposite the source 19. See, e.g., FIG. 3. However, detector 20 may also be positioned at other locations on the pipe 22 as needed to most effectively detect and/or receive radiation from the source 19. Detector 20 may be configured to receive a second amount of radiation from the source 19 after the first amount of radiation has passed through the section of the pipe 22. Detector 20 may then be configured to determine a composition of media flowing within the section of the pipe 22 based on the first and second amounts of radiation, and then send at least one measurement signal based on this determined composition via inbuilt signal conditioning software of detector 20 to software on an ROV attached to the apparatus 10 and/or directly to software located topside. In a particular embodiment, detector 20 may be configured to determine a density of the media flowing and/or stagnant within the section of the pipe 22. In a particular embodiment, detector 20 may weigh approximately fifteen pounds. In exemplary embodiments, detector 20 may be at least one of the MiniTrac 31 and MiniTrac 32 detectors for radiation-based density measurement offered by VEGA Americas, Inc. In this embodiment, detector 20 may include signal conditioning instruments and software such as the VEGAMET 624 which may power the MiniTrac 31 and process and display measured values such as the at least one measurement signal.

In various embodiments, detector 20 may make measurements of section of pipe 22 constantly at a high frequency. However, in some embodiments, due to the random nature of the radiation emitted from source 19, these measurements may be averaged and dampened via a multi-pass software filter in the detector 20 that changes the frequency of the update to the output based on the step change of sensed value. In an exemplary embodiment, apparatus 10 may increase its productivity from 1 to 20 ft/min, which equals up to 9.5 Km of pipeline/day.

In particular embodiments, more than one measurement of a section of pipe 22 may be taken by the apparatus 10 at one time. In some embodiments, it may be possible to include more than one detector 20 and/or if necessary, more than one source 19, to either sense a larger area on the pipe 22 and/or improve accuracy of the readings by the apparatus 10.

As shown in FIGS. 1 to 3, control canister 23 may be positioned on the main frame 12 of the apparatus 10 in a location below handle 36. Alternatively, control canister 23 may be located in an ROV attached to apparatus 10. In an exemplary embodiment, control canister 23 may include software configured to receive the at least one measurement signal from the detector 20, and convey the at least one measurement signal to software located in the ROV and/or to directly to software viewable and/or controlled by topside personnel. Software in the control canister 23 may be a Supervisory Control And Data Acquisition (SCADA) system used for remote monitoring and control that operates with coded signals over communication channels (using typically one communication channel per remote station). In various embodiments, software of control canister 23 may include a data acquisition (DAQ) system using coded signals over communication channels to acquire information about the status of remote equipment for display or for recording functions. In this embodiment, DAQ system in control canister 23 may include sensors, DAQ measurement hardware, and a computer with programmable software.

In particular embodiments, control canister 23 may include a local data acquisition board configured to receive and convey the at least one measurement signal to the software on ROV and/or software located topside and viewable and/or controlled by topside personnel. In this embodiment, control canister 23 may also include motor controllers for a propulsion drive and ballast drive, gyro, inclinometers, and/or an Ethernet to a signal conditioner (e.g., an RS232 signal conditioner). In alternative embodiments, control canister 20 may include other suitable configurations to assist in receiving and conveying the at least one measurement signal to software in the ROV and/or directly to software viewable and controlled by topside personnel. In an exemplary embodiment, control canister 23 may have a cylindrical shape. In an alternative embodiment, control canister 23 may have other shapes suitable for performing its receiving and conveying functions. In particular embodiment, control canister 23 may be made of titanium. Alternatively, control canister 23 may be made of other suitable materials. In an example embodiment, control canister 23 may include a DAQ system offered by National Instruments™.

In various embodiments, apparatus 10 may include at least one buoyancy structure 25 positioned on the main frame 12. At least one buoyancy structure 25 may be configured to hold the apparatus 10 in place on the pipe 22. In an exemplary embodiment, apparatus 10 may include two buoyancy structures 25 positioned on the main frame 12, with the control canister 23 positioned between the two buoyancy structures 25. See, e.g., FIG. 1. In exemplary embodiments, at least one buoyancy structure 25 may be made of foam. In alternative embodiments, at least one buoyancy structure 25 may be a ballast tank having variable or non-variable buoyancy control. In this embodiment, the ballast tank buoyancy structure 25 may be securable over a portion of the main frame 12.

In particular embodiments, apparatus 10 may further include a stabilizing system such as for e.g. a brick of lead positioned beneath the at least one buoyancy structure 25 and within the main frame 12. The brick of lead may be configured to act as a ballast assist in maintaining the stability of the apparatus 10 on the pipe 22. In this embodiment, the stabilizing system may include attachments to electric motors configured to move the brick of lead transversally within the apparatus 10. For example, if the apparatus 10 moves in an unwanted left or right direction once it is placed on the pipe 22, the electric motors may be used to move the brick of lead in the opposite direction to ensure proper balancing and positioning of the apparatus 10 on the pipe 22. In exemplary embodiments, stabilizing system may include attachments to inclinometers configured to measure angles of slope (or tilt), elevation, or depression of the apparatus 10 with respect to gravity, and thereby further assist in positioning the apparatus 10 on the pipe 22. In an exemplary embodiment, the inclinometers may be located within the control canister 23. In some embodiments, the apparatus 10 may also be securable to and positioned on the pipe 22 using hydraulic clamps or electrically operated via motor or electrical linear actuator.

Apparatus 10 may include at least one roller 18 attached to each opposing side of the main frame 12. At least one roller 18 may be configured to assist in moving the apparatus 10 along the pipe 22. In a particular embodiment, apparatus 10 may include two rollers 18 attached to each opposing side of the main frame 12. See, e.g., FIG. 3. In exemplary embodiments, at least one roller 18 may be made of rubber such as for e.g., urethane rubber. In this embodiment, apparatus 10 may include hydraulic or electric motors connected to at least one roller 18 and configured to rotate at least one roller 18 and move the apparatus 10 along the pipe 22. In an alternative embodiment, at least one roller 18 may not be motorized and apparatus 10 may be mechanically moved along the pipe 22. In some embodiments, apparatus 10 may also include at least two crawlers 16 positioned beneath ends and/or sides of the apparatus 10. See, e.g., FIG. 2. At least two crawlers 16 may be configured to work in tandem with at least one roller 18 to assist in faster and more efficient movement of the apparatus 10 along the pipe 22. In various embodiments, at least two crawlers 16 may either be motorized or non-motorized.

In exemplary embodiments, apparatus 10 may include a handle 36 mounted on the main frame 12. Handle 36 may be configured to provide for manipulation and placement of the apparatus 10 via an arm of the ROV or by manual manipulation. In some embodiments, apparatus 10 may also include secondary handles 37 on either a front end, back end, and/or sides of the main frame 12. Secondary handles 37 may act as a contingency for the ROV to move the apparatus 10 along the pipe 22 if the motorized rollers 18 and/or crawlers 16 are not functioning properly.

In some embodiments, a distance counter 27 may be attached to the apparatus 10. Distance counter 27 may be configured to measure and control the speed and distance traveled by the apparatus 10. Distance counters 27 or distance measuring wheels may be used to efficiently and quickly measure distances traveled by apparatus 10 attached to distance counter 27 and/or other tools/apparatuses attached to the distance counter 27. In exemplary embodiments, the distance counter 27 may be connected by a signal cable to the control canister 23, which may then send the measurement information to software on an ROV and/or directly to topside personnel. In exemplary embodiments, this functionality of the distance counter 27 may be incorporated into a propulsion drive circuit, where an encoder used as feedback for closed loop speed control of the drive may also be utilized for distance traveled data.

In embodiments, apparatus 10 may be attached to an ROV by connecting an ROV attachment 38 to an arm of the ROV, thereby allowing the ROV to move the apparatus 10 along pipe 22. In exemplary embodiments, the apparatus 10 may be moved along the pipe 22 at variable speeds ranging from approximately one to twenty feet per minute, depending on the content of the pipe 22, and the nature of any blockage within the pipe 22. Attachment 38 may include electrical, hydraulic, and/or signal connections or lines within the attachment 38 that connect the ROV to the apparatus 10, and vice-versa. Hydraulic lines of attachment 38 may be configured to control the several hydraulic connections discussed herein, including the hydraulic clamps. Electrical lines of attachment 38 may be configured to provide power to run the measurement apparatus 10 (and disclosed parts requiring electric power, including the electric motors and propulsion). Measurement apparatus 10 may include a battery or may alternatively be run using main power from the ROV. In an exemplary embodiment, the signal connections may include for e.g. fiber optic cables configured to convey the various measurement signals discussed herein from the control canister 22 to software located topside via an Ethernet connection. In embodiments of the present disclosure, apparatus 10 may be autonomous, semi-autonomous, or manually controlled. In the autonomous embodiment of the apparatus 10, apparatus 10 may be powered by a battery pack and/or connected wirelessly (e.g. Bluetooth) to the ROV or a vessel or monitoring system. In the manually controlled embodiment, apparatus 10 may be controlled by via a diver or an ROV attached to an attachment 38 of apparatus 10. In the semi-autonomous embodiment of the apparatus 10, apparatus 10 may include an acoustic modem or other equivalent device in combination with for e.g. attachment to an ROV.

Apparatus 10 may further include brushes 17 attached to the front end, back end, and/or sides of the main frame 12. Brushes 17 may be configured to clean debris and/or other material from the pipe 22 prior to measurement of the pipe 22. In an exemplary embodiment, three brushes 17 may be attached to an end of the main frame 12 that faces a forward direction of travel by the apparatus 10 along the pipe 22. See, e.g., FIG. 1. However, the apparatus 10 may include a greater or lesser number of brushes 17 necessary to clean the pipe 22 prior to being measured by apparatus 10. In some embodiments, trenches down either side of the pipeline/flowline 22 may be dredged using a jetter skid. In some embodiments, apparatus 10 may include a low pressure (approximately 120 psi greater than ambient pressure) centrifugal pump with nozzles immediately in front of the rollers/tracks 18 to clean the contact area.

Figure 4:
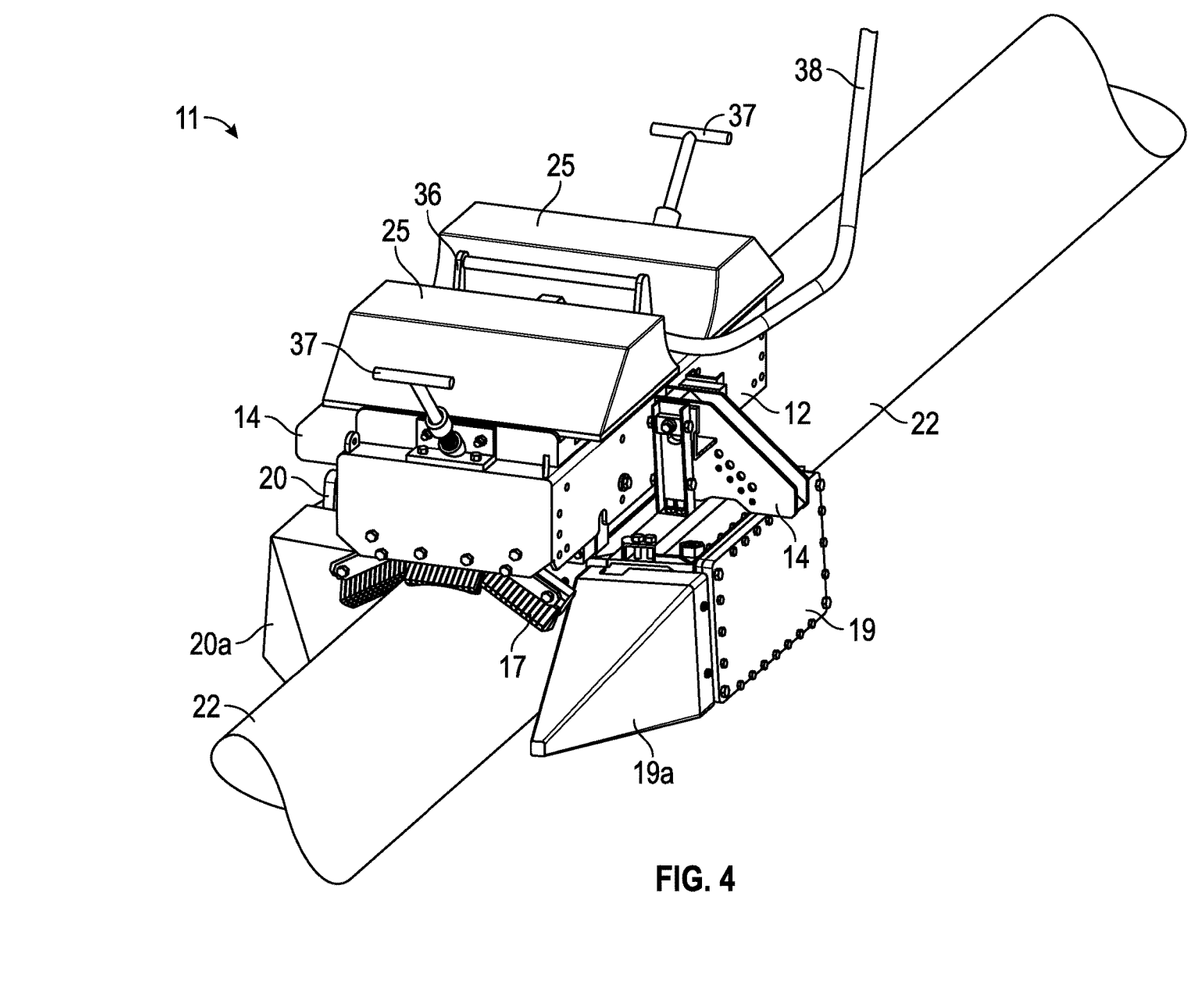
FIG. 4 is an isometric view of a measurement apparatus positioned on a section of pipe, according to an exemplary embodiment of the present disclosure.
Figure 5:
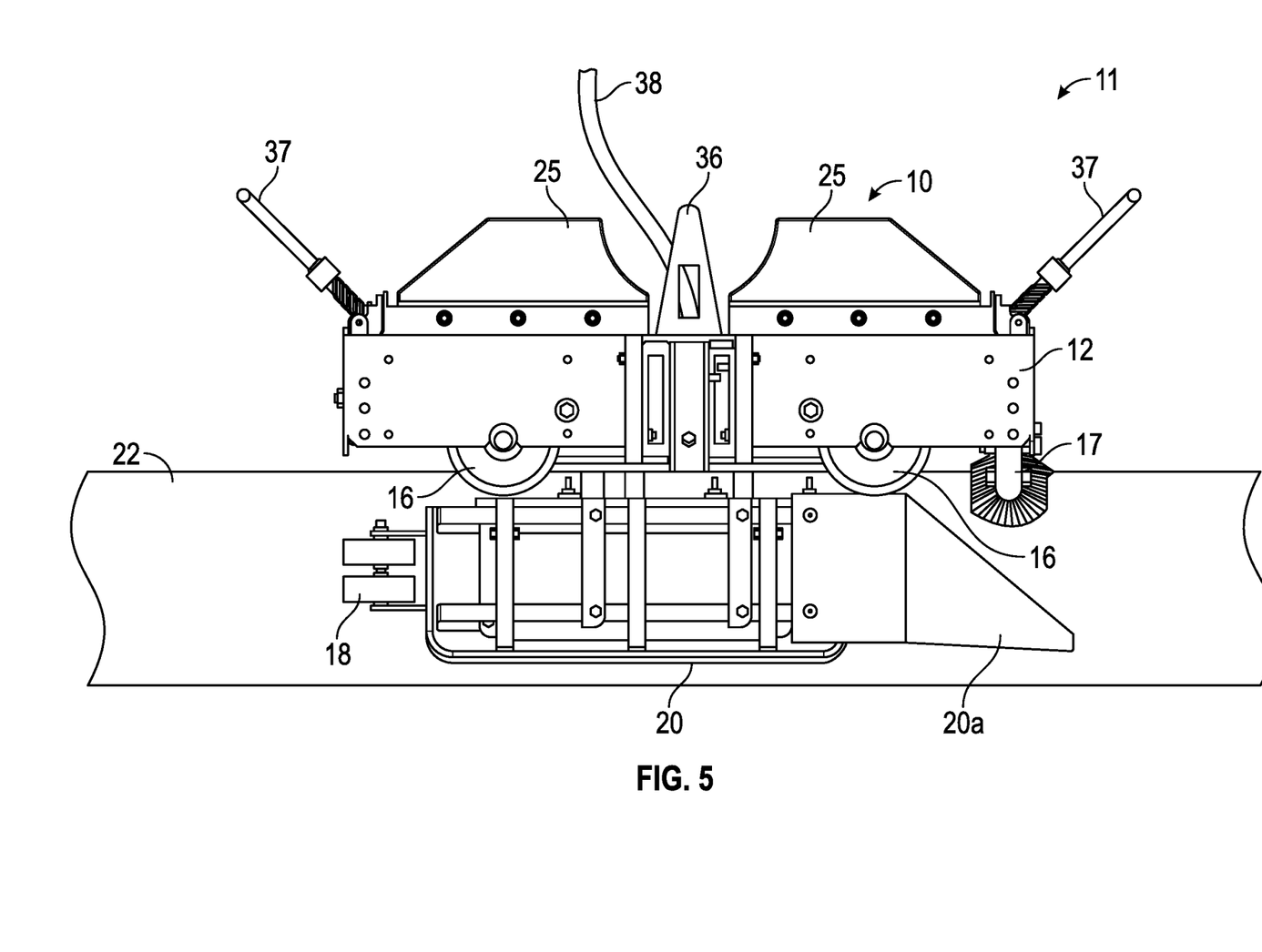
FIG. 5 is a side view of the measurement apparatus shown in FIG. 4.
Figure 6:
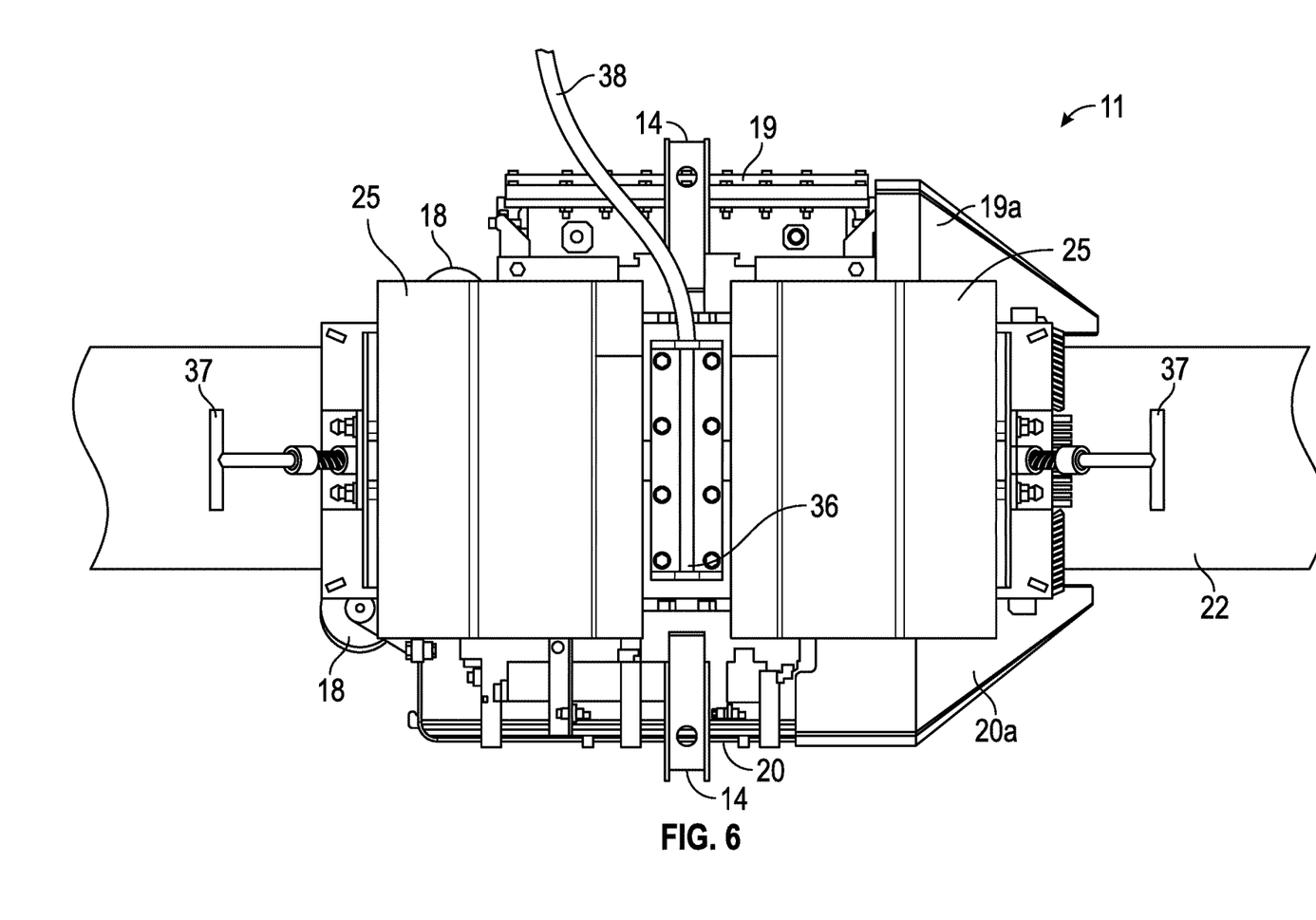
FIG. 6 is a top view of the measurement apparatus shown in FIG. 4.

Referring to FIGS. 4 to 6, different views of measurement apparatus 11 are shown. As shown, measurement apparatus 11 may have substantially the same features as apparatus 10 described herein, with some modifications. Particularly, apparatus 11 may include source 19, detector 20, cleaning structures 19a, 20a, elongated support frame 14, at least one buoyancy structure 25, brushes 17, at least one roller 18, and at least two crawlers 16 described herein, as well as attachment 38 described herein from apparatus 10 to an arm of an ROV for moving apparatus 10 along pipe 22. However, apparatus 11 may not include a control canister 23 positioned on the main frame 12 of apparatus 10. See, e.g., FIG. 5. Rather, control canister 23 may be located external to apparatus 11. For example, control canister 23 may be located at the ROV attached to apparatus 11. Embodiments of the present disclosure may also not include distance counters 27 to measure distance traveled by apparatus 11 since software in control canister 23 located in ROV attached to apparatus 11 may be used to perform this function.

Further, in this embodiment, at least one roller 18 may not be attached to the main frame 12; rather, at least one roller 18 may be attached directly to an end of the detector 20 carriage opposite cleaning structure 20a, and an end of the source 19 carriage opposite cleaning structure 19a. For example, two rollers may be attached to an end of each of source 19 and detector 20 at each opposing side of apparatus 11. See FIG. 5. Embodiments of the present disclosure may also include cleaning structures 19a, 20a having cone shapes but with more pointy edges than cleaning structures 19a, 20a of apparatus 10 to more efficiently move debris and other material away from the pipe 22. Embodiments of the present disclosure for apparatus 11 are not limited to these particular configurations and may include more or less features, including features described herein relating to apparatus 10.

Figure 7:
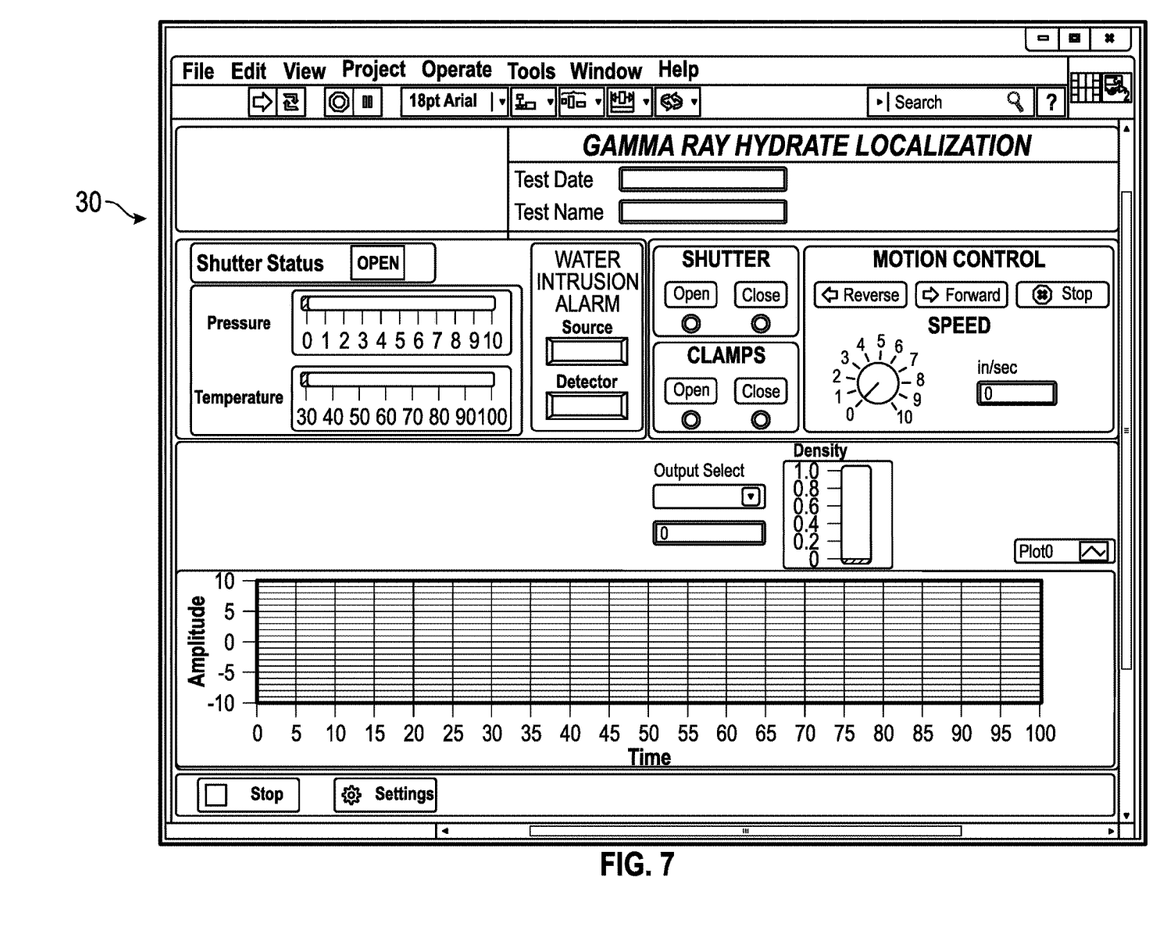
FIG. 7 is an illustration of a graphic user interface for software connected to a measurement apparatus and located topside, according to an exemplary embodiment of the present disclosure.

Referring now to FIG. 7, an illustration of a graphic user interface (GUI) for software 30 connected to a measurement apparatus 10, 11 and located topside is shown. Software 30 may receive the at least one measurement signal described herein from control canister 23 via an Ethernet or other suitable connection. FIG. 4 is simply an exemplary embodiment of the GUI for this software 30. In this exemplary embodiment, the software 30 may be a SCADA (Supervisory Control And Data Acquisition) system. Software 30 may provide a method to monitor, receive, save to a local hard drive on a computer topside, and/or display to topside personnel the at least one measurement signal, including for example, density and other composition data of a pipe 22, as well as other data related to apparatus 10, 11. GUI and/or software 30 may take other suitable forms necessary to provide relevant information regarding the apparatus 10, 11 and/or the composition of the pipe 22 to topside personnel viewing the GUI 30 and controlling the ROV and/or apparatus 10, 11. GUI 30 may include several indicators for topside personnel to easily manipulate and control the apparatus 10, 11, and to view the relevant density/composition in a section of the pipe 22.

In an exemplary embodiment, GUI 30 may include an "open" or "close" shutter status indicator for the shutter contained within the source 19. In this embodiment, the shutter being "open" indicates that radiation is being continuously transmitted from the source 19 via the collimator as described herein. The shutter being in the "close" position indicates that radiation is not being emitted from the source 19, and that it is safe for a diver to approach the apparatus 10, 11, if needed. Due to the particular importance and function of the shutter contained within the source 19, the GUI 30 may also include an additional identifier configured to flash a particular color. For example, the identifier may flash the color red if the shutter is in the "open" position to indicate that radiation is being transmitted from source 19. In an exemplary embodiment, the GUI 30 may include a water intrusion alarm for the source 19, detector 20, and/or control canister 23. This water intrusion alarm may also be configured to flash a particular color if water has somehow entered the source 19, detector 20, and/or control canister 23, thereby indicating a dangerous environment such that the measurement process must be immediately stopped.

In some embodiments, GUI 30 may include a motion control indicator allowing for topside personnel to control the speed and direction of the apparatus 10, 11. For example, the motion control indicator may be used to move the apparatus 10, 11 in reverse or forward directions along the pipe 22, stop the apparatus 10, 11, and/or set a fixed but variable speed of movement of the apparatus 10, 11. In an exemplary embodiment, GUI 30 may include indicators showing the pressure within apparatus 10, 11. GUI 30 may also include indicators showing the temperature within the source 19, detector 20, and/or control canister 23. If the indicator shows a dangerously high temperature, topside personnel may immediately stop the measurement process by closing the shutter. In some embodiments, GUI 30 may also include an "open" or "close" status indicator for the hydraulic clamps described herein.

In various embodiments, the GUI 30 may include several identifiers for properties of the section of pipe 22 being measured by the apparatus 10, 11, as well as identifiers relating to movement of the apparatus 10, 11. These identifiers may include but are not limited to outputs showing relevant density, percentage of density, distance traveled, time traveled, and amplitude. For example, GUI 30 may include a visual indicator for the density of the pipe 22 with values ranging from 0 to 1.0. See FIG. 7. In this exemplary embodiment, if the apparatus 10, 11 detects hydrates in the pipe 22, the value shown in the indicator may jump from 0 to 1. If the apparatus 10, 11 detects oil in the pipe 22, the value may jump from 0 to 0.8. If the apparatus 10, 11 detects wax in the pipe 22, the value may jump from 0 to 0.7. The relationship between these outputs may also be visually depicted using a graph. See, e.g., FIG. 4. The configuration of this particular GUI 30 and apparatus 10, 11 may therefore provide for an immediate Go/No Go indication using a few quick measurements of the section of pipe 22.

Figure 8:
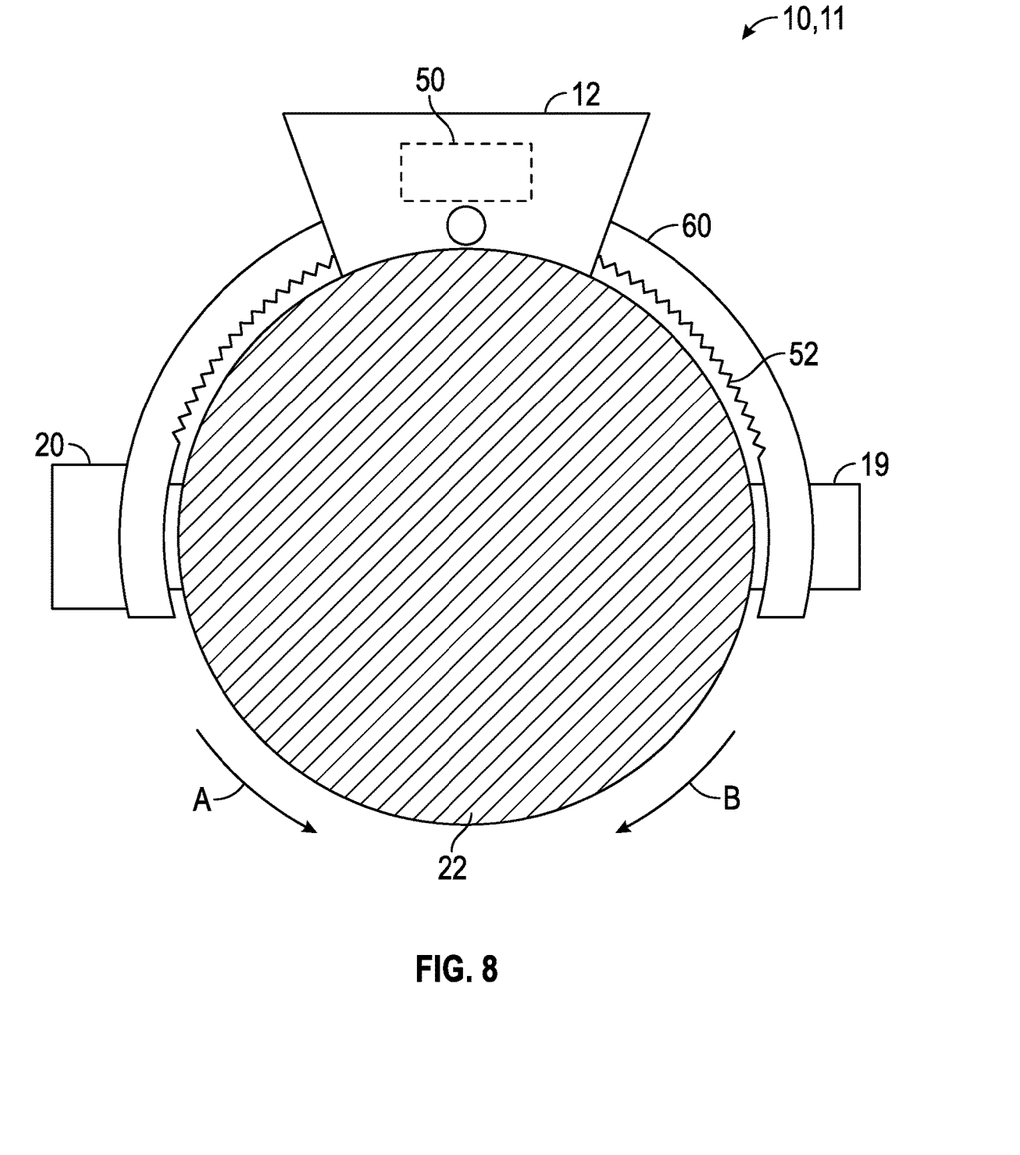
FIG. 8 is a front view of a measurement apparatus including a rotating plate positioned on a section of pipe, according to an exemplary embodiment of the present disclosure.

Referring to FIG. 8, an alternative embodiment of apparatus 10, 11 positioned on a section of pipe 22 is shown. In this embodiment, source 19 and detector 20 are shown as attached to opposing ends of a rotating plate 60 attached to the main frame 12 described herein. In some embodiments, hydraulic and/or electric motors 50 may be positioned within main frame 12 and attached to rotating plate 60 to actuate rotating plate 60. As shown, gears 32 may be located on an underside surface of rotating plate 60 adjacent to surface of pipe 22 and configured to assist hydraulic and/or electric motors 50 in rotation of plate 60 and attached source 19 and/or detector 20. In particular embodiments, source 19 and/or detector 20 may each rotate in a 180° angle (or a greater angle to assure more overlap of the area being measured) in both a counter-clockwise direction, A, and clockwise direction, B, to perform a multi-faceted 360° scan of a section of pipe 22 and measure composition of the section of pipe 22.

According to exemplary embodiments, methods are provided for the measurement of submerged surfaces. In an exemplary embodiment, a method includes attaching a measurement apparatus 10, 11 described herein to an ROV, and using the ROV to lower and place apparatus 10, 11 upon an exterior of a section of submerged pipeline 22. Measurement apparatus 10, 11 may have substantially the same features as measurement apparatuses 10, 11 described herein, including a main frame 12, source 19, detector 20, and/or control canister 23. Source 19 may then be used to transmit a continuous first amount of radiation towards the section of pipe 22. Detector 20 may then be used to receive and detect a second amount of radiation, determine a composition of the pipe 22 based on the first and second amounts of radiation, and create and send at least one measurement signal based on this composition of the pipe 22 to the control canister 23. Control canister 23 may be located on the main frame 12 of the apparatus 10, 11 or directly on the ROV attached to apparatus 10, 11. Control canister 23 may then be used to convey the at least one measurement signal to software on the ROV, which may then be outputted to software 30 located topside. Alternatively, control canister 23 may convey the at least one measurement signal directly to software 30 located topside. Once the section of pipe 22 is measured, additional measurements of the same section of pipe 22 may be made, and/or the apparatus 10, 11 may be moved along the pipe 22 using the ROV for measurement of another section of pipe 22.

Embodiments of the present disclosure may also be used in conjunction with the inspection apparatus having multiple pulsed eddy current (PEC) sensors disclosed in U.S. patent application Ser. No. 14/868,048, which is incorporated herein by reference. The PEC sensors may be configured to take measurements of a section of the pipeline 22 on which the inspection apparatus is placed and send multiple signals which are eventually converted into a single measurement signal for conveyance to an ROV. An average wall thickness of the section of the pipeline 22 may then be calculated from this measurement signal. In an exemplary embodiment, a second measurement of this section of pipe 22 may be taken using an ultrasonic sensor if the average wall thickness of the section of pipe 22 is below a desired amount. In some embodiments, this inspection apparatus may be placed adjacent to measurement apparatus 10, 11 described herein on a pipe 22 and both sets of measurements may be taken simultaneously. In alternative embodiments, at least one PEC sensor may be incorporated into an embodiment of the apparatus 10, 11 described herein (for example, within a side of the main frame 12) so as to take simultaneous multiple measurements of the pipe 22.

While the embodiments are described with reference to various implementations and exploitations, it will be understood that these embodiments are illustrative and that the scope of the disclosures is not limited to them. Many variations, modifications, additions, and improvements are possible. Further still, any steps described herein may be carried out in any desired order, and any desired steps may be added or deleted.

What is claimed is:
1. A measurement apparatus, comprising:
a main frame;

a source positioned outside a section of pipe located underwater and connected to the main frame, the source configured to transmit a continuous first amount of radiation;

a detector positioned outside the pipe and connected to the main frame at a location opposite the source, the detector configured to receive a continuous second amount of radiation, determine a composition of a media within the section of pipe based on the first amount of radiation and the second amount of radiation, and send at least one measurement signal;

a control system positioned on the main frame or on a remotely operated vehicle (ROV) attached to the apparatus, including a control canister having a data acquisition system (DAQ) configured to receive the at least one measurement signal from the detector and convey the at least one measurement signal to software located topside; and at least one buoyancy structure positioned on the main frame, the at least one buoyancy structure configured to hold the measurement apparatus in place on the pipe, wherein the measurement apparatus is configured to be at least one of autonomously, semi-autonomously, or manually controlled to be moved along the pipe and take multiple measurements of sections of the pipe;

wherein the measurement apparatus is configured to include a stabilizing system positioned beneath the at least one buoyancy structure and within the main frame, and configured to act as a ballast using electric motors configured to move the stabilizing system transversally within the main frame of the measurement apparatus to maintain the stability of the measurement apparatus on the pipe.

2. The measurement apparatus of claim 1, wherein the apparatus is autonomously controlled via at least a battery and wireless connections to the ROV.

3. The measurement apparatus of claim 1, wherein the apparatus is manually controlled via at least an underwater diver and the ROV.

4. A measurement apparatus, comprising:

a main frame;

a source positioned outside a pipe and connected to the main frame, the source configured to transmit a first amount of radiation;

a detector positioned outside the pipe and connected to the main frame at a location opposite the source, the detector configured to receive a second amount of radiation, determine a composition of a media within the pipe based on the first amount of radiation and the second amount of radiation, and send at least one measurement signal;

a control canister positioned on the main frame or on a remotely operated vehicle (ROV) attached to the measurement apparatus, the control canister configured to receive the at least one measurement signal from the detector and convey the at least one measurement signal to software located topside; and at least one buoyancy structure positioned on the main frame, the at least one buoyancy structure configured to hold the apparatus in place on the pipe;

wherein the measurement apparatus is configured to include a stabilizing system positioned beneath the at least one buoyancy structure and within the main frame, and configured to act as a ballast using electric motors configured to move the stabilizing system transversally within the main frame of the measurement apparatus to maintain the stability of the measurement apparatus on the pipe.

5. The measurement apparatus of claim 4, wherein the source and detector are each connected to the main frame using a support frame.

6. The measurement apparatus of claim 4, wherein the source and detector are each mounted within a source carriage and detector carriage, respectively.

7. The measurement apparatus of claim 6, further comprising at least one roller attached to at least one of each opposing side of the main frame and an end of each of the source carriage and detector carriage, respectively, the at least one roller configured to assist in moving the apparatus along the pipe.

8. The measurement apparatus of claim 6, further comprising a cleaning structure attached to a forward-direction facing end of at least one of the source carriage and detector carriage, the cleaning structure configured to move debris away from the pipe.

9. The measurement apparatus of claim 4, further comprising at least two crawlers positioned beneath the apparatus, the at least two crawlers configured to assist in moving the apparatus along the pipe.

10. The measurement apparatus of claim 4, further comprising a distance counter attached to the apparatus, the distance counter configured to measure and control the speed and distance traveled by the apparatus.

11. The measurement apparatus of claim 4, further comprising at least one brush attached to the apparatus, the at least one brush configured to clean debris on the pipe.

12. The measurement apparatus of claim 4, wherein the source includes a collimator to direct the first amount of radiation towards the pipe.

13. The measurement apparatus of claim 12, wherein the source includes a shutter to open or close the collimator.

14. The measurement apparatus of claim 13, wherein the source includes electric motors to activate the shutter.

15. The measurement apparatus of claim 4, wherein the control canister includes a data acquisition (DAQ) system configured to assist in receiving the at least one measurement signal from the detector and convey the at least one measurement signal to software located topside.

16. The measurement apparatus of claim 4, further comprising a handle mounted on the main frame, the handle configured to provide for manual or ROV-assisted manipulation and placement of the apparatus.

17. The measurement apparatus of claim 4, further comprising at least one sensor located within the main frame, the at least one sensor configured to take a measurement of the pipe and send at least one signal based on the measurement.

18. The measurement apparatus of claim 17, wherein the at least one sensor is a pulsed eddy current (PEC) sensor.

19. The measurement apparatus of claim 4, further comprising hydraulic clamps attached to the apparatus, the hydraulic clamps configured to attach the apparatus on the pipe.

20. The measurement apparatus of claim 19, further comprising at least one hydraulic line between the ROV and the apparatus, the at least one hydraulic line configured to activate the hydraulic clamps.

21. The measurement apparatus of claim 4, further comprising at least one electrical line between the ROV and the apparatus, the at least one electrical line configured to provide power to run the measurement apparatus.

22. The measurement apparatus of claim 4, wherein the first amount of radiation and the second amount of radiation include gamma rays.

23. The measurement apparatus of claim 22, wherein the gamma rays are derived from 137Cs.

24. A method for measuring submerged pipelines, comprising:
connecting an attachment of a measurement apparatus to a remotely operated vehicle (ROV), wherein the measurement apparatus comprises:
a main frame;
a source positioned outside a section of pipe and connected to the main frame, the source configured to transmit a first amount of radiation;
a detector positioned outside the section of pipe and connected to the main frame at a location opposite the source, the detector configured to receive a second amount of radiation, determine a composition of a media within the section of pipe based on the first amount of radiation and the second amount of radiation, and send at least one measurement signal;
a control canister positioned on the main frame or on the ROV, the control canister configured to receive the at least one measurement signal from the detector and convey the at least one measurement signal to software located topside; and
at least one buoyancy structure positioned on the main frame, the at least one buoyancy structure configured to hold the measurement apparatus in place on the pipe, lowering and placing the measurement apparatus upon the section of pipe using the ROV;
taking a measurement of the section of pipe using the detector to create the at least one measurement signal;
sending the at least one measurement signal from the detector to the control canister; and
conveying the at least one measurement signal from the control canister to the software located topside;
wherein the measurement apparatus is configured to include a stabilizing system positioned beneath the at least one buoyancy structure and within the main frame, and configured to act as a ballast using electric motors configured to move the stabilizing system transversally within the main frame of the measurement apparatus to maintain the stability of the measurement apparatus on the pipe.

25. The method of claim 24, further comprising moving the measurement apparatus to another section of the pipe using the ROV after each round of measurements.

26. A system, comprising:
a remotely operated vehicle (ROY); and
a measurement apparatus connected to the ROV, the measurement apparatus comprising:
a main frame;
a source positioned outside a section of pipe and connected to the main frame, the source configured to transmit a first amount of radiation;
a detector positioned outside the section of pipe and connected to the main frame at a location opposite the source, the detector configured to receive a second amount of radiation, determine a composition of a media within the section of pipe based on the first amount of radiation and the second amount of radiation, and send at least one measurement signal; and
a control canister positioned on the main frame or on the ROV, the control canister configured to receive the at least one measurement signal from the detector and convey the at least one measurement signal to software located topside,
wherein the measurement apparatus is configured to include a stabilizing system positioned beneath the at least one buoyancy structure and within the main frame, and configured to act as a ballast using electric motors configured to move the stabilizing system transversally within the main frame of the measurement apparatus to maintain the stability of the measurement apparatus on the pipe, and
wherein the software is configured such that a user may access the software to view the composition and other properties of the section of pipe and to control movement of the apparatus via the ROV.

* * * * *